(12) United States Patent
Chung

(10) Patent No.: US 11,530,414 B2
(45) Date of Patent: *Dec. 20, 2022

(54) GENE EXPRESSION CASSETTE AND EXPRESSION VECTOR INCLUDING THE SAME

(71) Applicant: CELL BIOTECH CO., LTD., Gimpo-si (KR)

(72) Inventor: Myung Jun Chung, Seoul (KR)

(73) Assignee: CELL BIOTECH CO., LTD., Gyeonggi-Do (KR)

( * ) Notice: Subject to any disclaimer, the term of this patent is extended or adjusted under 35 U.S.C. 154(b) by 377 days.

This patent is subject to a terminal disclaimer.

(21) Appl. No.: 16/471,872

(22) PCT Filed: Oct. 16, 2018

(86) PCT No.: PCT/KR2018/012157
§ 371 (c)(1),
(2) Date: Jun. 20, 2019

(87) PCT Pub. No.: WO2019/139227
PCT Pub. Date: Jul. 18, 2019

(65) Prior Publication Data
US 2019/0328800 A1    Oct. 31, 2019

(30) Foreign Application Priority Data
Jan. 9, 2018 (KR) .......... 10-2018-0003002

(51) Int. Cl.
| | |
|---|---|
| *A61K 35/747* | (2015.01) |
| *A61K 35/744* | (2015.01) |
| *A61K 35/745* | (2015.01) |
| *A61K 35/00* | (2006.01) |
| *C12N 15/74* | (2006.01) |
| *C12N 15/65* | (2006.01) |
| *C12R 1/23* | (2006.01) |
| *C12R 1/24* | (2006.01) |
| *C12R 1/245* | (2006.01) |

(52) U.S. Cl.
CPC .......... *C12N 15/746* (2013.01); *A61K 35/744* (2013.01); *A61K 35/745* (2013.01); *A61K 35/747* (2013.01); *C12N 15/65* (2013.01); *A61K 2035/115* (2013.01); *C12N 2840/55* (2013.01); *C12R 2001/23* (2021.05); *C12R 2001/24* (2021.05); *C12R 2001/245* (2021.05)

(58) Field of Classification Search
None
See application file for complete search history.

(56) References Cited

U.S. PATENT DOCUMENTS

| | | | |
|---|---|---|---|
| 5,837,509 A | 11/1998 | Israelsen et al. | |
| 11,117,953 B2 * | 9/2021 | Chung | .......... C12N 1/205 |
| 2010/0112655 A1 | 5/2010 | Paul | |
| 2015/0265660 A1 | 9/2015 | Kaznessis et al. | |

FOREIGN PATENT DOCUMENTS

| | | |
|---|---|---|
| JP | 3553065 B2 | 8/2004 |
| KR | 10-0985702 B1 | 10/2010 |
| WO | 2014/037505 A1 | 3/2014 |

OTHER PUBLICATIONS

Shields HE Electroporation of Pediococcus pentosaceus and the curing rate of plasmids. May 2006, Thesis—Utah State University, pp. 1-16, 2006.*
GenBank: CP006854.1, Jan. 31, 2014, 362 pages.
International Search Report and Written Opinion issued for International Application No. PCT/KR2018/012157, dated Feb. 1, 2019, 11 pages.

* cited by examiner

*Primary Examiner* — S. Devi
(74) *Attorney, Agent, or Firm* — Hamre, Schumann, Mueller & Larson, P.C.

(57) ABSTRACT

The present invention relates to a gene expression cassette including a strong promoter derived from lactic acid bacteria, and a gene expression vector including the same. According to the present invention, a large amount of a human protein, the physiological activity of which has been verified, may be stably produced with high efficiency by introducing a useful foreign gene into an expression vector and transforming probiotics with the expression vector. Through the production of this protein, it is possible to provide a basis for developing functional probiotics and making products using them.

13 Claims, 7 Drawing Sheets
Specification includes a Sequence Listing.

| P8 protein secretion | |
|---|---|
| Promoter | ug/L |
| ChoS | 66.3±1.3 |
| G6PI | 121.4±5.9 |
| GK | 139.0±11.2 |
| L-ldh | 138.6±24.0 |
| PK | 137.3±9.7 |
| ErmE | 75.1±11.8 |
| 6PFK | 72.8±30.5 |

Promoter name

ChoS: choline ABC transpoter permease promoter
G6PI: glucose-6-phosphate isomerase promoter
GK: glucokinase promoter
L-ldh: L-lactate dehydrogenase promoter
PK: pyruvate kinase promoter
ErmE: erythromycin E
6PFK: 6-phosphofructokinase promoter

| P8 protein secretion | |
|---|---|
| Two promoter system | ug/L |
| PKCOSP8-PKoriP8 | 466.6 |
| PKCOSP8-PKCOSP8 | 192.0 |
| PKCOSP8-ChoSoriP8 | 100.2 |
| GKCOSP8-PKoriP8 | 281.0 |
| GKCOSP8-GKoriP8 | 196.3 |
| GKCOSP8-L-ldhoriP8 | 68.2 |

SEQUENCE LISTING

<160> NUMBER OF SEQ ID NOS: 11

<210> SEQ ID NO 1
<211> LENGTH: 324
<212> TYPE: DNA
<213> ORGANISM: Artificial Sequence
<220> FEATURE:
<223> OTHER INFORMATION: Primer ChoS

<400> SEQUENCE: 1

```
ggatccgtga tgtacgtaag aaagatttac gtcaaatcac aacggccgta ggtgacggtg      60
gcgtcgctgg acaacaagcg tatgaatata ttcaagcttt aaatgattaa agtcaaaata     120
agccacggtg aaaaccgggg cttttctttt tgccaaaatt caaaaagtga ttggtctata     180
cctaaaatta aaaaaacgct ttctggtatt ccatgggtat tgtataatga agtaactat     240 aagttacatc ataggaggac ttttgaatga aaaaaaagat tatctcagct attttaatgt    300
ctacagtgat actttctgct gcag                                            324
```

<210> SEQ ID NO 2
<211> LENGTH: 184
<212> TYPE: DNA
<213> ORGANISM: Artificial Sequence
<220> FEATURE:
<223> OTHER INFORMATION: Promotor Erm

<400> SEQUENCE: 2

```
ggatccttttt tagtattttt aattaattgt aatcagcaca gttcattatc aaccaaacaa     60
aaaataagtg gttataatga atcgttaata agcaaaattc atataaccaa attaaagagg    120
gttataatga aaaaaaagat tatctcagct attttaatgt ctacagtgat actttctgct    180
gcag                                                                  184
```

<210> SEQ ID NO 3
<211> LENGTH: 324
<212> TYPE: DNA
<213> ORGANISM: Artificial Sequence
<220> FEATURE:
<223> OTHER INFORMATION: Primer PK

<400> SEQUENCE: 3

```
ggatccctaa agatcgcgtt ttagcaagta agatgggtgc ttacgctgtt gagctactcc     60
ttgaaggtaa gggtggttta gcagttggaa tcttagaaaa taaggttcaa gctcataaca    120
tgcttgactt gtttgatgca aaacatcaag cagatgattc actttaccaa ttaagtgaag    180
atttatcatt ctagagttct attaatattt ggataaaatg acttaagaag tcttttataa    240
tttaaaatca agggagagat tctgtaatga aaaaaaagat tatctcagct attttaatgt    300
ctacagtgat actttctgct gcag                                            324
```

<210> SEQ ID NO 4
<211> LENGTH: 324
<212> TYPE: DNA
<213> ORGANISM: Artificial Sequence
<220> FEATURE:
<223> OTHER INFORMATION: Primer GK

<400> SEQUENCE: 4

```
ggatccataa tctggtaaat tagttgagat ggtattatga aaacacttta tgatgtgcaa     60
caacttttaa agcaattcgg aatatttgtt tacgttggaa aacgtaaatg ggatattgaa    120
ttgatgagta ttgaattgaa aaatttgtac aaagcaggag tcgtcgataa accgacttat    180
```

```
gttaaagctc agttggtttt acgacatgag catcatattg aagaggttag agataaccaa    240
caaaaataat ggagggtttc gaagtaatga aaaaaaagat tatctcagct attttaatgt    300
ctacagtgat actttctgct gcag                                          324
```

<210> SEQ ID NO 5
<211> LENGTH: 324
<212> TYPE: DNA
<213> ORGANISM: Artificial Sequence
<220> FEATURE:
<223> OTHER INFORMATION: Primer G6Pi

<400> SEQUENCE: 5

```
ggatccatgc cggctaaagt ggtggataaa ttgaatcatc cccaagaact ggaataagat    60
aaaattgtag tgctttcagg ctttaccagc catcttttga aaaaattaat ttctttcaaa    120
agtgcgtgtg acaggtgatc aactagatta aatggggagg gtatcccagt aaatattagg    180
ttaaatcgga taggcttaac caaattaagt aattttattg tataatggta cagataaaga    240
attttaaaca aaggggtag ttattaatga aaaaaaagat tatctcagct attttaatgt     300
ctacagtgat actttctgct gcag                                          324
```

<210> SEQ ID NO 6
<211> LENGTH: 324
<212> TYPE: DNA
<213> ORGANISM: Artificial Sequence
<220> FEATURE:
<223> OTHER INFORMATION: Primer 6PFK

<400> SEQUENCE: 6

```
ggatccccag ttattttagt ttatgaggat actaatgaac ataatgagtt gtctgaaaaa    60
ttttatttaa atgacagttc tgaagtaaaa gaacaattag cagaattgct aggaagtcaa    120
catatttcgt taattaaaaa ataaattttg aataaagcac ttacattcga ttaattaaga    180
aaatggtaca gacaactgtt ttcaaaagtg ataaaatcaa caatgaagtt ttgaaaaaac    240
tcaatatttc tgtttgaggt gaaagatga aaaaaaagat tatctcagct attttaatgt     300
ctacagtgat actttctgct gcag                                          324
```

<210> SEQ ID NO 7
<211> LENGTH: 324
<212> TYPE: DNA
<213> ORGANISM: Artificial Sequence
<220> FEATURE:
<223> OTHER INFORMATION: Primer L-LDH

<400> SEQUENCE: 7

```
ggatcctcat ttcatgtta tttttccacc ctcaacacgc aaaaacggct gaaagagcaa     60
aaacccctca gctgtccacg tttatttca tgtaatatta ccatattatt gaccccaagc     120 gggtcttta acctctaact tatcaatcac tttactaact atacccgaac ttcataaaat     180
ttttactcaa ctttctttta tgaaaatgct atacttagta ttgtttgata aattcaaata    240
ttatatgaaa aaaggggatt gatcttatga aaaaaaagat tatctcagct attttaatgt    300
ctacagtgat actttctgct gcag                                          324
```

<210> SEQ ID NO 8
<211> LENGTH: 324
<212> TYPE: DNA
<213> ORGANISM: Artificial Sequence
<220> FEATURE:

<223> OTHER INFORMATION: Primer D-LDH

<400> SEQUENCE: 8

| | | | | |
|---|---|---|---|---|
| ggatcccagt | tcaattaatt | tattttgaat | cgtttgataa | tcagcatgac gcaatgtctg | 60 |
| cagaatatca | gttcaagcaa | cgaacgcgaa | gtagtaagat | taaatttctt aaaaagaatg | 120 |
| gtatttcatt | aacaaattta | aaataatagt | ggtacagtta | aggcaattaa cgactaattt | 180 |
| aatagcttga | atactgtaat | attttttgaa | tcatgataca | gtatgtaaaa caaattattt | 240 |
| agccaagtct | gagaggagaa | ttttgatga | aaaaaagat | tatctcagct attttaatgt | 300 |
| ctacagtgat | actttctgct | gcag | | | 324 |

<210> SEQ ID NO 9
<211> LENGTH: 4757
<212> TYPE: DNA
<213> ORGANISM: Artificial Sequence
<220> FEATURE:
<223> OTHER INFORMATION: Plasmid pCBT24-2

<400> SEQUENCE: 9

| | | | | | |
|---|---|---|---|---|---|
| aagttaatgt | aagccttaag | gtttcaacta | aagcaattac | ggtcaaccat aaccatagta | 60 |
| ttggattgtc | attttattgg | ctataaaata | gtaaatcagt | gaatttcatt ggatccgcta | 120 |
| aagatcgcgt | tttagcaagt | aagatgggtg | cttacgctgt | tgagctactc cttgaaggta | 180 |
| agggtggttt | agcagttgga | atcttagaaa | ataaggttca | agctcataac atgcttgact | 240 |
| tgtttgatgc | aaaacatcaa | gcagatgatt | cactttacca | attaagtgaa gatttatcat | 300 |
| tctagagttc | tattaatatt | tggataaaat | gacttaagaa | gtcttttata atttaaaatc | 360 |
| aagggagaga | ttctgtaatg | aaaaaaaaga | ttatctcagc | tattttaatg tctacagtga | 420 |
| tactttctgc | tgcagccccg | ttgtcaggtg | tttacgctga | agtaattatt atggctaccg | 480 |
| ttgatccaga | aaagactcta | ttccttgatg | aaccaatgaa | taaagttttt gattggtcta | 540 |
| acagtgaggc | tccggtgcga | gatgccttat | gggattacta | tatggaaaag aatagccgtg | 600 |
| acacgatcaa | aacagaagaa | gaaatgaaac | ctgtattaga | tatgtcagat gacgaagtta | 660 |
| aagcattagc | ggagaaagtc | ttgaaaaagt | aacctgacaa | gaaccagtct gctattgata | 720 |
| gactatttt | gtccgtgaaa | tcctcgcgta | tttccgtgag | gagcatagta tatttagcga | 780 |
| tcttcaaatt | ttaagtatat | tgattcatat | gtttatcctc | ctaagtttga ggacaaatcg | 840 |
| gattccacgg | cctcaatgac | tgagctccgc | ctatttttat | aggttaatgt catgataata | 900 |
| atggtttctt | agcgattcac | aaaaaatagg | cacacgaaaa | acaagttaag ggatgcagtt | 960 |
| tatgcatccc | ttaacttact | tattaaataa | tttatagcta | ttgaaaagag ataagaattg | 1020 |
| ttcaaagcta | atattgttta | atcgtcaat | tcctgcatgt | tttaaggaat tgttaaattg | 1080 |
| attttttgta | atatttttct | tgtattcttt | gttaacccat | ttcataacga aataattata | 1140 |
| cttttgttta | tctttgtgtg | atattcttga | tttttttcta | cttaatctga taagtgagct | 1200 |
| attcacttta | ggtttaggat | gaaaatattc | tcttggaacc | atacttaata tagaaatatc | 1260 |
| aacttctgcc | attaaaagta | atgccaatga | gcgttttgta | tttaataatc ttttagcaaa | 1320 |
| cccgtattcc | acgattaaat | aaatctcatt | agctatacta | tcaaaacaa ttttgcgtat | 1380 |
| tatatccgta | cttatgttat | aaggtatatt | accatatatt | ttataggatt ggttttagg | 1440 |
| aaatttaaac | tgcaatatat | ccttgttaa | aacttggaaa | ttatcgtgat caacaagttt | 1500 |
| attttctgta | gttttgcata | atttatggtc | tatttcaatg | gcagttacga aattacacct | 1560 |
| ctttactaat | tcaagggtaa | aatggccttt | tcctgagccg | atttcaaaga tattatcatg | 1620 |

```
ttcatttaat cttatatttg tcattatttt atctatatta tgttttgaag taataaagtt    1680
ttgactgtgt tttatatttt tctcgttcat tataaccctc tttaatttgg ttatatgaat    1740
tttgcttatt aacgattcat tataaccact tattttttgt ttggttgata atgaactgtg    1800
ctgattacaa ttaattaaaa atactaaaaa tgcccatatt ttttcctcct tataaaatta    1860
gtataattat agcacgaaaa ggatctaggt gaagatcctt tttgataatc tcatgaccaa    1920
aatcccttaa cgtgagtttt cgttccactg agcgtcagac cccgtagaaa agatcaaagg    1980
atcttcttga gatccttttt ttctgcgcgt aatctgctgc ttgcaaacaa aaaaaccacc    2040
gctaccagcg gtggtttgtt tgccggatca agagctacca actcttttc cgaaggtaac    2100 tggcttcagc agagcgcaga taccaaatac tgttcttcta gtgtagccgt agttaggcca    2160
ccacttcaag aactctgtag caccgcctac atacctcgct ctgctaatcc tgttaccagt    2220
ggctgctgcc agtggcgata agtcgtgtct taccgggttg gactcaagac gatagttacc    2280
ggataaggcg cagcggtcgg gctgaacggg ggttcgtgc acacagccca gcttggagcg    2340
aacgacctac accgaactga gatacctaca gcgtgagcta tgagaaagcg ccacgcttcc    2400
cgaagggaga aaggcggaca ggtatccggt aagcggcagg gtcggaacag gagagcgcac    2460
gagggagctt ccagggggaa acgcctggta tctttatagt cctgtcgggt ttcgccacct    2520
ctgacttgag cgtcgatttt tgtgatgctc gtcaggggg cggagcctat ggaaaaacgc    2580
cagcaacgcg gcctttttac ggttcctggc cttttgctgg ccttttgctc acatgttctt    2640
tcctgcgtta tccctgatt ctgtggataa ccgtattacc gcctttgagt gagctgatac    2700
cgctcgccgc agccgaacga ccgagcgcag cgagtcagtg agcgaggaaa tcgatactga    2760
attggcgaaa gccaaagttt ctataaaacc ttgctttcct gcttaacggc gagtgaaaaa    2820
gcggttaagc tggctcagct tggacgggt tcgggcgtt agcgtccgta ttaaatgtgg    2880
cttaccataa ccaacgaaca gagtgaggtg caaggagctg tgcgactgga gtttaatgtg    2940
agccggtttt tggctcactc ctttgtgttt tttgtttcta gattttaatc tcgtacagcg    3000
gtgcctcttt tatacctctt ttataaacct cttttaaacc tctttagac ccctcttgag    3060 ccttactctc ccaaggctca cagaaggtta tcaagtacct tttgtctgtt tatcaagtac    3120
cttttgtctg tttatcaagt accttttgtc tgtttatcaa gtaccttttg tctgtttatc    3180 aagtacctt ataagttctg tacttgataa aaaggtactt ttattttaat atgtgtttga    3240
ggtgataatc atggctaatg agttagttaa gtatgatcct gagttgaata ctattccctt    3300
gagaaaattt accccaattg agatgaattt attttttca attatttccc gcatgcggga    3360
tcaagggaat aaaactgttc gtttctcttt tgaccagtta aaagagctta gtaactataa    3420
accaaccgca aataaacgtt ttattgatga tattgaaaat acataccaaa agatcctcag    3480
ccttaggttt ggccgtagaa gtaagagtgg cttaaatcgt gaattttttg ttatgtttac    3540
tgaatttgaa attaaaggtg aagctgaaga accttatgtt gatattcaga tttatcccaa    3600
agcattgcac ttgctaaacg atttagaaag ttgggttcgt tatgccctaa cagaatttag    3660
aaatttaaaa agcagttacg ctaaaacaat gtttcgtcta attaagcaat tcgaactac    3720 tggctattct tatttctcta aagaagattt ttttgaattg cttgatatac ctaaaagtta    3780
ttggaatagt ccttcaaagg ttgacaaaaa ggttattaag ccaattagag aagaattaac    3840
cccgcttttt agagggctaa cgattagaaa aaaatatggt aaaggcagag gaaaaccagt    3900
tatcggttat tctttacttt ggaaacctga aagcaaggac gcaaatgatt tttctcaagg    3960
```

```
caaatttcaa gatgagcgtc aaaaactctt taacattcag cacaatgatg aattatcaga    4020
taaagaaaag tggcgtgcaa ttgacaaagt taaatgcttg cctttaggaa caactgaaaa    4080
acaggtactg gctgaaaaac aagctgaaca tgatcaaaaa atcagagatc aagcaagaca    4140
agaatttctc gctgatctcc gaaagggggtt ttaaaatcat gtctaaaact attagagaac    4200
ttgctgatga attgaatgtc tccaaacaga ctattcaata tcactaccaa agactaccag    4260
caaagaacca acaaaagaat agtcagggca caaaccttat tagtcctaca gcagaaagaa    4320
ttataagaag caaggtagca aagcctttgc tagcaaaaaa acagcaaaga ggtagcaaag    4380
aattgccaaa gactagcaaa gaaaataatg atctggttgc tactctgaga agagaagtag    4440
aagatttaaa ggctcaacgt gacaaacagc ttgctaccaa agaccgacaa atagaccatc    4500
taacaaaatt ggtggatcag cagcaacaat tacaattagc aacagtagca gataaccgtc    4560
gattaaaaga tcatgtacaa aagctaagtg ggcaactaac tcaaaaaact aacgacaact    4620
tgtcgaccgg aaatgatctt tttaacatcc aagataaaga agcaaaata gctaaacaga    4680 agattgttaa atctggtagt aataaagatg gcatacacac aaatagagct attaaacgtt    4740
ggtggaaatt ctggtaa                                                  4757
```

<210> SEQ ID NO 10
<211> LENGTH: 234
<212> TYPE: PRT
<213> ORGANISM: Artificial Sequence
<220> FEATURE:
<223> OTHER INFORMATION: P8 protein

<400> SEQUENCE: 10

```
Gly Ala Ala Gly Thr Ala Ala Thr Thr Ala Thr Thr Ala Thr Gly Gly
1               5                   10                  15

Cys Thr Ala Cys Cys Gly Thr Thr Gly Ala Thr Cys Cys Ala Gly Ala
                20                  25                  30

Ala Ala Ala Gly Ala Cys Thr Cys Thr Ala Thr Thr Cys Cys Thr Thr
                35                  40                  45

Gly Ala Thr Gly Ala Ala Cys Cys Ala Ala Thr Gly Ala Ala Thr Ala
    50                  55                  60

Ala Ala Gly Thr Thr Thr Thr Thr Gly Ala Thr Thr Gly Gly Thr Cys
65              70                  75                  80

Thr Ala Ala Cys Ala Gly Thr Gly Ala Gly Gly Cys Thr Cys Cys Gly
                85                  90                  95

Gly Thr Gly Cys Gly Ala Gly Ala Thr Gly Cys Cys Thr Thr Ala Thr
                100                 105                 110

Gly Gly Gly Ala Thr Thr Ala Cys Thr Ala Thr Ala Thr Gly Gly Ala
            115                 120                 125

Ala Ala Ala Gly Ala Ala Thr Ala Gly Cys Cys Gly Thr Gly Ala Cys
    130                 135                 140

Ala Cys Gly Ala Thr Cys Ala Ala Ala Cys Ala Gly Ala Ala Ala Gly
145                 150                 155                 160

Ala Ala Gly Ala Ala Ala Thr Gly Ala Ala Ala Cys Cys Thr Gly Thr
                165                 170                 175

Ala Thr Thr Ala Gly Ala Thr Ala Thr Gly Thr Cys Ala Gly Ala Thr
                180                 185                 190

Gly Ala Cys Gly Ala Ala Gly Thr Thr Ala Ala Ala Gly Cys Ala Thr
                195                 200                 205

Thr Ala Gly Cys Gly Gly Ala Gly Ala Ala Ala Gly Thr Cys Thr Thr
        210                 215                 220
```

```
Gly Ala Ala Ala Ala Ala Gly Thr Ala Ala
225                 230

<210> SEQ ID NO 11
<211> LENGTH: 122
<212> TYPE: PRT
<213> ORGANISM: Artificial Sequence
<220> FEATURE:
<223> OTHER INFORMATION: p14 Protein

<400> SEQUENCE: 11

Ala Lys Ser Gln Asp Gln Phe Asn Glu Lys Ala Gly Lys Lys Ile Thr
1               5                   10                  15

Val Ser Asp Glu Ala Val Asp Lys Ala Ala Lys Lys Ile Glu Gln Val
                20                  25                  30

Gly Tyr Val Thr Glu Lys Asp Val Pro Glu Met Ile Asp Arg Asp Tyr
            35                  40                  45

Thr Arg Ala Leu Ser Lys Lys Val Ser Ala Lys Leu His Gln Asp Lys
        50                  55                  60

Asp Asp Asp Tyr Phe Tyr Glu Glu Pro Phe Asp Tyr Glu Asn Gly Arg
65                  70                  75                  80

Ile Ala Asn Ile Ile Trp Asp Met Asp Lys Ile Lys Thr Arg Glu Glu
                85                  90                  95

Ala Met Lys Thr Leu Ala Asn Glu Leu Gly Leu Thr Val Pro Lys Ile
            100                 105                 110

Val Met Arg Lys Val Asp Glu Gln Val Phe
            115                 120
```

GENE EXPRESSION CASSETTE AND EXPRESSION VECTOR INCLUDING THE SAME

STATEMENT AS TO GOVERNMENT-FUNDED RESEARCH

This invention was made with Korean Government support under a grant No. S2367890 funded by the Ministry of Trade, Industry and Energy, under the supervision of the Republic of Korea Small and Medium Business Administration, from the WC300 project for developing drug-delivery probiotics for treatment of inveterate interstinal disease, study period was 2016.02.01-2020.12.31.

TECHNICAL FIELD

The present invention relates to a gene expression cassette for producing a useful protein and an expression vector including the same, and more specifically to a novel gene expression cassette, including a promoter, a secretion signal peptide and a selective marker gene, which is used to efficiently express a foreign gene, and an expression vector including the same.

BACKGROUND ART

The production of biologically active polypeptides and proteins is economically important for the production of pharmaceutical preparations for human and veterinary use, enzymes, and other specific chemicals. Recombinant DNA techniques that use bacterial cells, fungal cells or mammalian cells as expression hosts are a particularly useful tool for producing large quantities of polypeptides.

In general, the recombinant production of a desired protein includes a process of transfecting host cells with an expression vector including a signal which, when operably linked to a gene encoding the protein, regulates expression of the gene. The transfected cells are grown under conditions suitable for expression of the recombinant protein.

For a recombinantly-produced protein intended for commercial use, it is particularly desirable to express a high level of desired protein from the host cell. As the amount of desired protein produced per cell is increased, the volume of cells to be grown to obtain a predetermined amount of the product is reduced, and thus the production cost can be reduced. In addition, since the desired protein occupies a larger portion of the total protein produced by the host cells, the desired protein can be easily purified. Accordingly, an expression-regulating signal capable of expressing a high level of desired protein is required.

In recent years, studies have been actively conducted to produce large amounts of high-value-added substances beneficial to the human body by use of microorganisms, especially lactic acid bacteria. If a gene expression cassette capable of expressing a high level of foreign gene in lactic acid bacteria is developed, it will advantageously be used in the food field, the medical and pharmaceutical field, and other industrial fields.

DISCLOSURE

Technical Problem

The present invention has been made to meet the above-mentioned technical requirements, and one object of the present invention is to provide a gene expression cassette including a promoter which has strong promoter activity in lactic acid bacteria.

Another object of the present invention is to provide an expression vector including a gene expression cassette which includes the promoter operably linked to a heterologous nucleic acid.

Still another object of the present invention is to provide a host cell including the expression vector of the present invention.

Still another object of the present invention is to provide a microbial strain including the expression vector of the present invention.

Technical Solution

One aspect of the present invention to achieve the above-described objects is directed to a gene expression cassette including: at least one promoter operably linked to a heterologous nucleic acid encoding a biologically active polypeptide and selected from the group consisting of SEQ ID NO: 1 (Chos promoter), SEQ ID NO: 2 (ermE promoter), SEQ ID NO: 3 (PK promoter), SEQ ID NO: 4 (GK promoter), SEQ ID NO: 5 (G6Pi promoter), SEQ ID NO: 6 (6PFK promoter), SEQ ID NO: 7 (L-LDH promoter), and SEQ ID NO: 8 (D-LDH promoter); a secretion signal peptide; and a selective marker gene.

The gene expression cassette may further include, downstream of the promoter, a second promoter, a second secretion signal peptide, and a second heterologous nucleic acid sequence. The second promoter may be the same as or different from the first promoter, and the second heterologous nucleic acid sequence may be the same as or different from the first heterologous nucleic acid sequence.

The selective marker gene may be an antibiotic-resistant gene.

The secretion signal peptide may be a USP45 secretion signal peptide, Usp45 N4 or a *Lactobacillus brevis* S-layer protein signal peptide.

The gene expression cassette of the present invention may further include a replication origin replicable in a strain.

Another aspect of the present invention to achieve the above-described objects is directed to an expression vector including the gene expression cassette.

Still another aspect of the present is directed to a strain transformed with the expression vector of the present invention. The microbial strain may be a strain belonging to the genus *Lactobacillus, Latococcus, Leuconostoc, Pediococcus,* or *Bifidobacterium*.

Advantageous Effects

In the present invention, a novel gene expression cassette and expression vector have been developed, which can highly express a foreign gene by a promoter structure that works in probiotics. The expression vector including the gene expression cassette of the present invention can produce a high level of exogenous protein in probiotics, and thus may be widely used for the production of food proteins or pharmaceutical proteins.

The gene expression cassette of the present invention can efficiently enrich cells, which express a high level of foreign gene introduced therewith, by drug selection, and can shorten the task of establishing a high-expression cell line. Accordingly, a cell expression system employing the gene expression cassette of the present invention will be used as a biomedicine, and will highly contribute to the development of new drugs, and the like.

MODE FOR INVENTION

Figure 1:
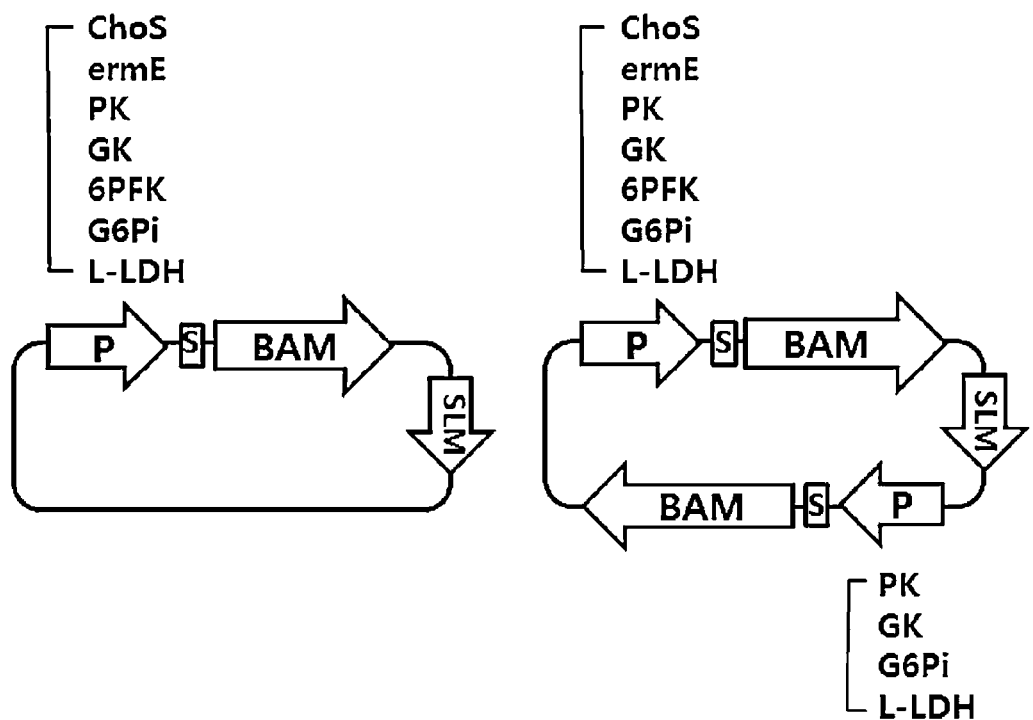
FIG. 1 is a view showing the configuration of a gene expression cassette according to one embodiment of the present invention.

The present invention will be described in more detail below with reference to the accompanying drawings.

Unless otherwise defined, all the scientific and technical terms used herein have the same meanings as commonly understood by those skilled in the art to which the present invention pertains. Dictionary of Microbiology and Molecular Biology, Singleton et al., $2^{nd}$ edition, John Wiley and Sons (New York), provides a general guide to many of the terms used herein.

The term "nucleic acid" refers to a deoxyribonucleotide or ribonucleotide polymer in either single- or double-stranded form, and unless otherwise limited, encompasses known analogs of natural nucleotides that that hybridize to nucleic acids in a manner similar to naturally occurring nucleotides. Unless otherwise indicated, a particular nucleic acid sequence includes its complementary sequence.

A "gene expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally, transcription termination signals. Typically, the gene expression cassette includes a nucleic acid to be transcribed (e.g., a heterologous nucleic acid encoding a desired polypeptide), and a promoter. Additional factors necessary or helpful in effecting expression may also be used as described herein.

As used herein, the term "promoter" refers to a DNA sequence capable of controlling the expression of a coding sequence or functional RNA. Any person skilled in the art will easily recognize a promoter region. The promoter consists of proximal and more distal upstream elements. Promoter proximal elements include a TATA box capable of directing RNA polymerase II to initiate RNA synthesis at an appropriate transcription initiation site. Distal elements include regulatory sequences often referred to as enhancers, which are additional regulatory elements that are involved in tissue-specific or time-specific expression upstream of the TATA box. Accordingly, an enhancer is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even include synthetic DNA segments. It is understood by those skilled in the art that different promoters may direct the expression of a gene in different tissues or cell types, or at different stages of development.

The term "biologically active molecule (BAM)" refers to substances which are involved in gene therapy or capable of regulating immune responses, and include substances capable of regulating intracellular signal transduction mechanisms or the expression of other particular genes. These substances may include growth factors, substances for cancer treatment, tumor suppressors, cytokines, interferons, and the like.

As used herein, a "heterologous sequence" or a heterologous nucleic acid" means one that originates from a foreign source (or species) or, if originates from the same source, is modified from its original foam. Thus, a heterologous nucleic acid operably linked to a promoter is derived from a source different from that from which the promoter was derived, or, if derived from the same source, is modified from its original form. Modification of the heterologous sequence may occur, for example, by treating the DNA with a restriction enzyme to generate a DNA fragment that is capable of being operably linked to the promoter.

The term "operably linked" refers to functional linkage between a nucleic acid expression control sequence (such as a promoter, signal sequence, or array of transcription factor binding sites) and a heterologous nucleic acid sequence, wherein the expression control sequence affects transcription and/or translation of the nucleic acid corresponding to the heterologous nucleic acid sequence.

As used herein, the term "expression vector" refers to a vector capable of expressing a desired exogenous protein in a host cell, and refers to a vector containing essential regulatory elements to which a gene insert is operably linked in such a manner as to be expressed. Proper expression vectors include a signal sequence or leader sequence for membrane targeting or secretion, in addition to expression control sequences such as a promoter, an operator, an initiation codon, a termination codon, a polyadenylation signal and an enhancer, and may be prepared in various manners depending on the intended use. The expression vector of the present invention may include a selectable marker for selecting a host cell containing the vector.

The term "downstream" refers to a nucleotide sequence that is located 3' to a reference nucleotide sequence. In particular, downstream nucleotide sequences generally relate to sequences that follow the starting point of transcription. For example, the translation initiation codon of a gene is located downstream of the start site of transcription.

The term "upstream" refers to a nucleotide sequence that is located 5' to a reference nucleotide sequence. In particular, upstream nucleotide sequences generally relate to sequences that are located on the 5' side of a coding sequence or starting point of transcription. For example, most promoters are located upstream of the start site of transcription.

The terms "restriction endonuclease" and "restriction enzyme" may be used interchangeably, and refer to enzymes that a specific nucleotide sequence in a double-stranded DNA.

As used herein, "P8 protein (Protein No. 8)" refers to an 8-KDa protein having an amino acid sequence of SEQ ID NO: 10, extracted from lactic acid bacteria (*Lactobacillus rhamnosus*).

As used herein, "P14 protein (Protein No. 14)" refers to a 14-KDa protein having an amino acid sequence of SEQ ID NO: 11, extracted from lactic acid bacteria (*Lactobacillus rhamnosus*).

As used herein, the term "cystatin" refers to substances that inhibit the activity of intracellular proteases. Cystatins are currently classified into intracellular family I (cystatin A, and cystatin B), secretory family II (cystatin C, cystatin D, cystatin S, egg white cystatin, and milk cystatin), and family III (kininogens). Cystatin A is present in epithelial tissues such as epidermis, digestive tracts and vagina, as well as leukocytes, and protects the body from the invasion of pathogens, and cystatin B is found inmost cytoplasm and acts to prevent viral infection by inhibiting the activity of proteases. Egg white cystatin also helps prevent viral infection, and cystatin C is known to play an important role in the defense function of the immune system.

As shown in FIG. 1, one embodiment of the present invention is directed to a gene expression cassette including: at least one promoter operably linked to a heterologous nucleic acid encoding a biologically active polypeptide and selected from the group consisting of SEQ ID NO: 1 (Chos promoter), SEQ ID NO: 2 (ermE promoter), SEQ ID NO: 3 (PK promoter), SEQ ID NO: 4 (GK promoter), SEQ ID NO: 5 (G6Pi promoter), SEQ ID NO: 6 (6PFK promoter), SEQ ID NO: 7 (L-LDH promoter), and SEQ ID NO: 8 (D-LDH promoter); a secretion signal peptide; and a selective marker gene.

TABLE 1

| Abbreviation of promoter name | Sequence (5' -> 3') |
|---|---|
| ChoS (SEQ ID ON: 1) | GGATCCGTGATGTACGTAAGAAAGATTTACGTCAAATCACA ACGGCCGTAGGTGACGGTGGCGTCGCTGGACAACAAGCGTA TGAATATATTCAAGCTTTAAATGATTAAAGTCAAAATAAGC CACGGTGAAAACCGGGGCTTTTCTTTTTGCCAAAATTCAAA AAGTGATTGGTCTATACCTAAAATTAAAAAAACGCTTTCTG GTATTCCATGGGTATTGTATAATGAAAGTAACTATAAGTTA CATCATAGGAGGACTTTTGAATGAAAAAAAAGATTATCTCA GCTATTTTAATGTCTACAGTGATACTTTCTGCTGCAG |
| ErmE (SEQ ID ON: 2) | GGATCCTTTTTAGTATTTTTAATTAATTGTAATCAGCACAG TTCATTATCAACCAAACAAAAAATAAGTGGTTATAATGAAT CGTTAATAAGCAAAATTCATATAACCAAATTAAAGAGGGTT ATAATGAAAAAAAAGATTATCTCAGCTATTTTAATGTCTAC AGTGATACTTTCTGCTGCAG |
| PK (SEQ ID ON: 3) | GGATCCCTAAAGATCGCGTTTTAGCAAGTAAGATGGGTGCT TACGCTGTTGAGCTACTCCTTGAAGGTAAGGGTGGTTTAGC AGTTGGAATCTTAGAAAATAAGGTTCAAGCTCATAACATGC TTGACTTGTTTGATGCAAAACATCAAGCAGATGATTCACTT TACCAATTAAGTGAAGATTTATCATTCTAGAGTTCTATTAA TATTTGGATAAAATGACTTAAGAAGTCTTTTATAATTTAAA ATCAAGGGAGAGATTCTGTAATGAAAAAAAAGATTATCTCA GCTATTTTAATGTCTACAGTGATACTTTCTGCTGCAG |

TABLE 1-continued

| Abbreviation of promoter name | Sequence (5' -> 3') |
|---|---|
| GK (SEQ ID ON: 4) | GGATCCATAATCTGGTAAATTAGTTGAGATGGTATTATGAA AACACTTTATGATGTGCAACAACTTTTAAAGCAATTCGGAA TATTTGTTTACGTTGGAAAACGTAAATGGGATATTGAATTG ATGAGTATTGAATTGAAAAATTTGTACAAAGCAGGAGTCGT CGATAAACCGACTTATGTTAAAGCTCAGTTGGTTTTACGAC ATGAGCATCATATTGAAGAGGTTAGAGATAACCAACAAAAA TAATGGAGGGTTTCGAAGTAATGAAAAAAAAGATTATCTCA GCTATTTTAATGTCTACAGTGATACTTTCTGCTGCAG |
| G6Pi (SEQ ID ON: 5) | GGATCCATGCCGGCTAAAGTGGTGGATAAATTGAATCATCC CCAAGAACTGGAATAAGATAAAATTGTAGTGCTTTCAGGCT TTACCAGCCATCTTTTGAAAAAATTAATTTCTTTCAAAAGT GCGTGTGACAGGTGATCAACTAGATTAAATGGGGAGGGTAT CCCAGTAAATATTAGGTTAAATCGGATAGGCTTAACCAAAT TAAGTAATTTTATTGTATAATGGTACAGATAAAGAATTTTA AACAAAAGGGGTAGTTATTAATGAAAAAAAAGATTATCTCA GCTATTTTAATGTCTACAGTGATACTTTCTGCTGCAG |
| 6PFK (SEQ ID ON: 6) | GGATCCCCAGTTATTTTAGTTTATGAGGATACTAATGAACA TAATGAGTTGTCTGAAAAATTTTATTTAAATGACAGTTCTG AAGTAAAAGAACAATTAGCAGAATTGCTAGGAAGTCAACAT ATTTCGTTAATTAAAAAATAAATTTTGAATAAAGCACTTAC ATTCGATTAATTAAGAAAATGGTACAGACAACTGTTTTCAA AAGTGATAAAATCAACAATGAAGTTTTGAAAAAACTCAATA TTTCTGTTTGAGGTGAAAAGATGAAAAAAAAGATTATCTCA GCTATTTTAATGTCTACAGTGATACTTTCTGCTGCAG |
| L-LDH (SEQ ID ON: 7) | GGATCCTCATTTTCATGTTATTTTTCCACCCTCAACACGCA AAAACGGCTGAAAGAGCAAAAACCCCTCAGCTGTCCACGTT TATTTTCATGTAATATTACCATATTATTGACCCCAAGCGGG TCTTTTAACCTCTAACTTATCAATCACTTTACTAACTATAC CCGAACTTCATAAAATTTTTACTCAACTTTCTTTTATGAAA ATGCTATACTTAGTATTGTTTGATAAATTCAAATATTATAT GAAAAAAGGGGATTGATCTTATGAAAAAAAAGATTATCTCA GCTATTTTAATGTCTACAGTGATACTTTCTGCTGCAG |
| D-LDH (SEQ ID ON: 8) | GGATCCCAGTTCAATTAATTTATTTTGAATCGTTTGATAAT CAGCATGACGCAATGTCTGCAGAATATCAGTTCAAGCAACG AACGCGAAGTAGTAAGATTAAATTTCTTAAAAAGAATGGTA TTTCATTAACAAATTTAAAATAATAGTGGTACAGTTAAGGC AATTAACGACTAATTTAATAGCTTGAATACTGTAATATTTT TTGAATCATGATACAGTATGTAAAACAAATTATTTAGCCAA GTCTGAGAGGAATTTTTGATGAAAAAAAAGATTATCTCA GCTATTTTAATGTCTACAGTGATACTTTCTGCTGCAG |

The gene expression cassette of the present invention is a DNA set necessary for expressing a biologically active protein encoded by a foreign gene in probiotic cells, and includes a heterologous nucleic acid encoding a biologically active polypeptide, and a promoter that promotes expression of the heterologous nucleic acid. Of the promoters of SEQ ID NO: 1 to SEQ ID NO: 8, six (Chos promoter, ermE promoter, PK promoter, GK promoter, G6Pi promoter, and 6PFK promoter) selected from the glycolysis metabolic pathway, and two (L-LDH promoter and D-LDH promoter) were selected from the secondary metabolite lactate production pathway.

Referring to FIG. 1, the promoter included in the gene expression cassette of the present invention acts to increase the expression and secretion levels of a physiologically active substance in lactic acid bacteria and is one derived from *Pediococcus pentosaceus*. In FIG. 1, P represents a promoter; S represents a secretion signal peptide; BAM represents a heterologous nucleic acid encoding a biologically active material; and SLM represents a selective labeling marker.

The gene expression cassette may increase not only the expression level of a heterologous nucleic acid, but also the secretion level thereof. The expression "protein is secreted" used herein means that the protein is transported extracellularly from microbial cells, and this expression includes the case in which the entire protein molecule is substantially present in medium in a completely released form, and also includes the case in which the entire protein molecule is present in the cell surface layer, and the case in which a portion of the protein molecule is present in medium while the remaining portion of the molecule is present in the cell surface layer.

In order to direct an exogenous protein, expressed by the expression vector of the present invention, into the secretion pathway of the host cells, a secretion signal peptide (S) may be provided in the gene expression cassette. The secretion signal peptide sequence is usually located at the 5' end of the DNA sequence encoding the exogenous protein.

The expression vector of the present invention may also include a replication origin replicable in probiotics cells. The reason for this is that manipulation of the vector is more efficient in probiotics or bacteria strains, and preferred examples of the replication origin include ColE1, Ori, oriT, and the like.

It is possible to increase the total production of a recombinant protein in many systems by inducing the secretion of a protein expressed from probiotics. In the present invention, the secretion signal peptide may include a secretion signal peptide that directs strong protein secretion, such as a USP45 secretion signal, Usp45 N4 in which lysine at position 4 of a wild-type Usp45 secretion signal is substituted with asparagine, or a *Lactobacillus brevis* S-layer protein signal peptide.

In the present invention, the heterologous nucleic acid may be a gene encoding a hormone, a cytokine, an enzyme, a coagulation factor, a transporter protein, a receptor, a regulatory protein, a structural protein, a transcription factor, an antigen, an antibody or the like. Specific examples thereof include, but are not limited to, genes encoding thrombopoietin, growth hormones, growth hormone-releasing hormones, growth hormone-releasing peptides, interferons, interferon receptors, colony-stimulating factors, glucagon-like peptides (GLP-1, etc.), G-protein-coupled receptors, interleukins, interleukin receptors, enzymes, interleukin binding proteins, cytokine binding proteins, macrophage activators, macrophage peptides, B-cell factors, T-cell factors, protein A, allergy inhibitors, necrosis glycoproteins, immunotoxins, lymphotoxins, tumor necrosis factors, tumor suppressors, transforming growth factors, α-1 anti-trypsin, albumin, α-lactalbumin, apolipoprotein-E, erythropoietin, highly glycosylated erythropoietin, angiopoietin, hemoglobin, thrombin, thrombin receptor activating peptides, thrombomodulin, blood factors VII, VIIa, VIII, IX and XIII, plasminogen activators, fibrin-binding peptides, urokinases, streptokinases, hirudin, protein C, C-reactive proteins, superoxide dismutase, leptin, platelet-derived growth factors, epithelial growth factors, epidermal growth factors, angiostatin, angiotensin, bone growth factors, bone stimulating proteins, calcitonin, insulin, atriopeptin, cartilage inducing factors, elcatonin, connective tissue activating factors, follicle stimulating hormones, luteinizing hormones, luteinizing hormone releasing hormones, nerve growth factors, parathyroid hormones, relaxin, secretin, somatomedin, insulin-like growth factors, adrenocortical hormones, glucagon, cholecystokinin, pancreatic polypeptides, gastrin releasing peptides, corticotropin releasing factors, thyroid stimulating hormones, autotaxin, lactoferrin, myostatin, receptors, receptor antagonists, cell surface antigens, virus derived vaccine antigens, monoclonal antibodies, polyclonal antibodies, antibody fragments, and the like.

For example, in the present invention, heterologous nucleic acids may encode growth factors, such as proteins involved in the regulation of cell division, neurotrophic factors (brain-derived neurotrophic factor, glial cell derived neurotrophic factor, NGF, NT3, NT4 and NT5), cytokines (α-, β- or γ-interferon, interleukin such as IL-1 or IL-2, tumor necrosis factor or insulin-like factor I or II), protein kinases (MAP kinase), protein dehydrogenases, and cell receptors for such factors.

The heterologous nucleic acid may preferably encode a therapeutic peptide or a disease-related polypeptide. In addition, the heterologous nucleic acid may encode an antigenic polypeptide for use as a vaccine. Such antigenic polypeptides are preferably derived from pathogens, such as microorganisms or viruses, or tumors.

The gene expression cassette of the present invention includes a selective labeling marker (SLM) that makes it possible to select bacterial cells containing the desired construct. The term "selective labeling marker" refers to an identifying factor, usually an antibiotic or chemical resistance gene, that is able to be selected for based upon the marker gene's effect, i.e., resistance to an antibiotic, resistance to a herbicide, colorimetric markers, enzymes, fluorescent markers, and the like. Examples of selectable marker genes known and used in the art include, but are not necessarily limited to, genes providing resistance to ampicillin, neomycin, streptomycin, gentamycin, kanamycin, hygromycin, chloramphenicol, erythromycin, bialaphos herbicide, sulfonamide, and the like; and genes that are used as phenotypic markers, i.e., anthocyanin regulatory genes, isopentanyl transferase gene, and the like.

When the selective labeling marker and the heterologous nucleic acid are placed on the same vector, the two may be adjacent to each other, or a spacer sequence may also be inserted therebetween. The selective labeling marker may be located either upstream or downstream of the heterologous nucleic acid, but when they are inserted adjacent to each other, the heterologous nucleic acid is preferably located downstream of the selective labeling marker.

A single vector may also include two or more selective labeling markers. The selective labeling markers may be antibiotic resistance genes, and in this case, the same antibiotic resistance markers may be selected, or different antibiotic resistance markers may also be selected.

The vector of the present invention is constructed such that it can express a target protein and also includes a secretion signal peptide capable of inducing extracellular secretion of the expressed protein. In particular, the vector of the present invention can provide remarkable advantages in that it can be applied to lactic acid bacteria that are ingested in everyday life, unlike currently commercialized yeast and *E. coli* systems which are used for the purpose of expression and secretion only.

The gene expression cassette of the present invention may be synthesized by a known technique described in the literature (see the document, Carruthers et al., Cold Spring Harbor Symp. Quant. Biol. 47: 411-418 (1982), and the document, Adams et al., J. Am. Chem. Soc. 105: 661 (1983)). Thereafter, double-stranded DNA fragments may be obtained either by synthesizing the complementary strand and annealing the strands together under appropriate conditions, or by adding the complementary strand using DNA polymerase with an appropriate primer sequence.

In the present invention, the order of arrangement of the promoter, the secretion signal peptide, the heterologous nucleic acid, and the selective labeling marker is not particularly limited as long as the expression of the selective marker gene is possible. However, generally, the promoter, the secretion signal peptide, the heterologous nucleic acid, and the selective labeling marker are sequentially arranged in order from an upstream location to a downstream location. These four elements do not need to be linked directly to one another, and may optionally include an intron, a spacer sequence, an enhancer, etc. therebetween.

In another embodiment of the present invention as shown in FIG. 1, the gene expression cassette may further include, downstream of the promoter, a second promoter other than the above-described promoter of any one of SEQ ID NO: 1 to SEQ ID NO: 8, a second secretion signal peptide, and a second nucleic acid sequence encoding a biologically active polypeptide.

In another embodiment of the present invention, the gene expression cassette necessarily has a first promoter upstream of the heterologous nucleic acid to be expressed, and may also include a second promoter downstream of the heterologous nucleic acid to be expressed. The first promoter and the second promoter may be the same as or different from each other. It is possible to use not only a non-specific promoter capable of promoting the expression of a foreign gene in most cells or tissues, but also a specific or selective promoter, such as a tissue- or organ-specific promoter, a tumor-specific promoter, a development- or differentiation-specific promoter or the like. For example, a specific promoter may be used as the first promoter, and a non-specific promoter may be used as the second promoter.

Still another aspect of the present invention is directed to an expression vector including the gene expression cassette for expression of a foreign according to the present invention. This expression vector includes a gene cassette for introducing a gene into the chromosome of a host cell.

The expression vector including the gene expression cassette of the present invention may be a plasmid vector. However, without being limited thereto, for example, a virus vector, a cosmid vector, bacterial artificial (BAC), yeast artificial chromosome (YAC) and other non-plasmid vectors may also be used. Examples of this vector include plasmids, virus vectors, such as adenovirus (Ad) vectors, adeno-associated virus (AAV) vectors, lentivirus vectors, retrovirus vectors, Herpes virus vectors, Sendai virus vector and the like, non-virus vectors such as biodegradable polymers, and the like.

The expression vector of the present invention may include two promoters. Namely, it may further include, downstream of the first promoter, a second promoter, a second secretion signal peptide, and a second nucleic acid sequence encoding a biologically active polypeptide. This expression vector can increase the expression and secretion levels of an exogenous protein compared to an expression vector including a single promoter.

Figure 2:
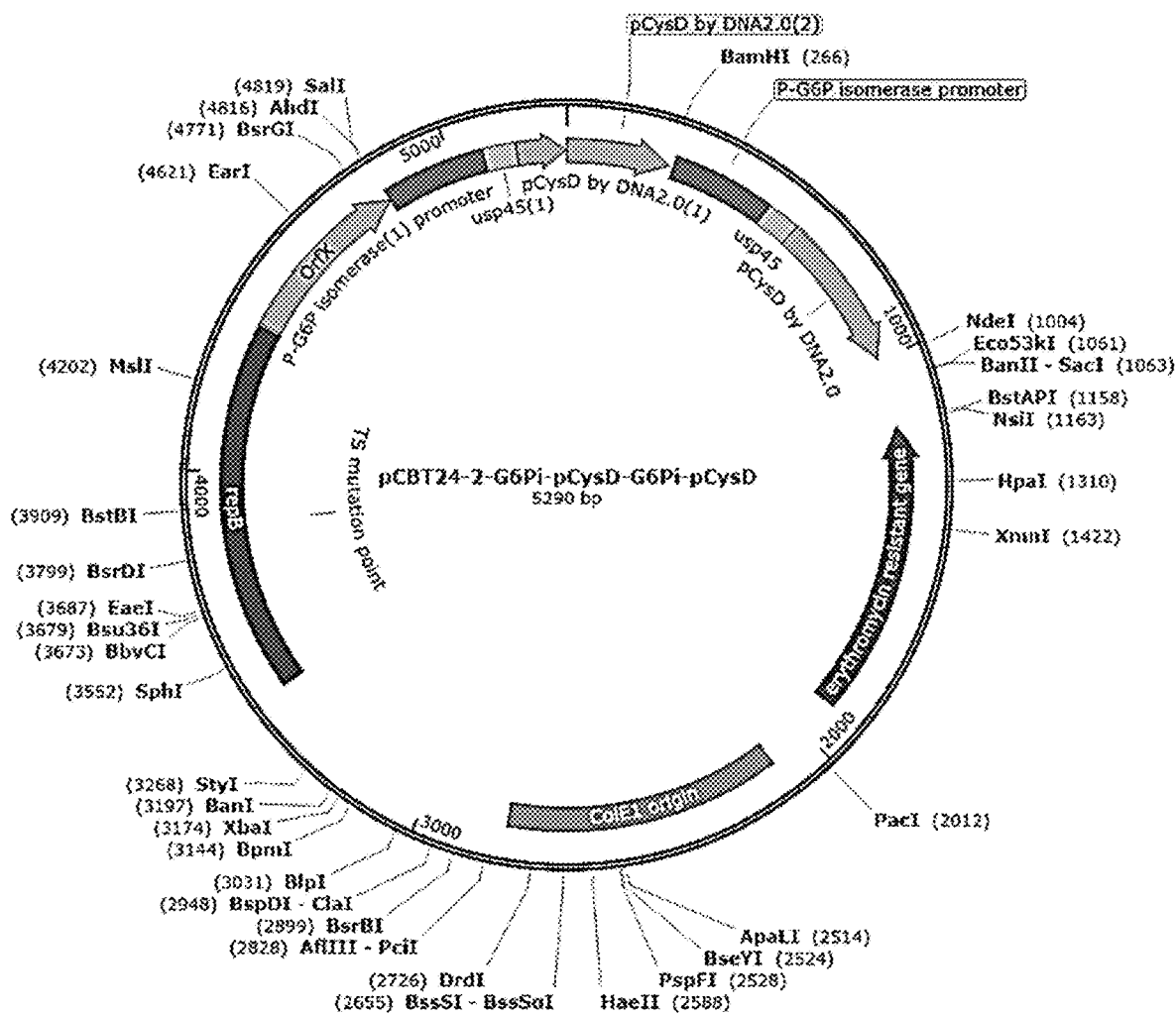
FIG. 2 is a cleavage map of an expression vector (pCBT24-2-CysA) according to one embodiment of the present invention.
Figure 3:
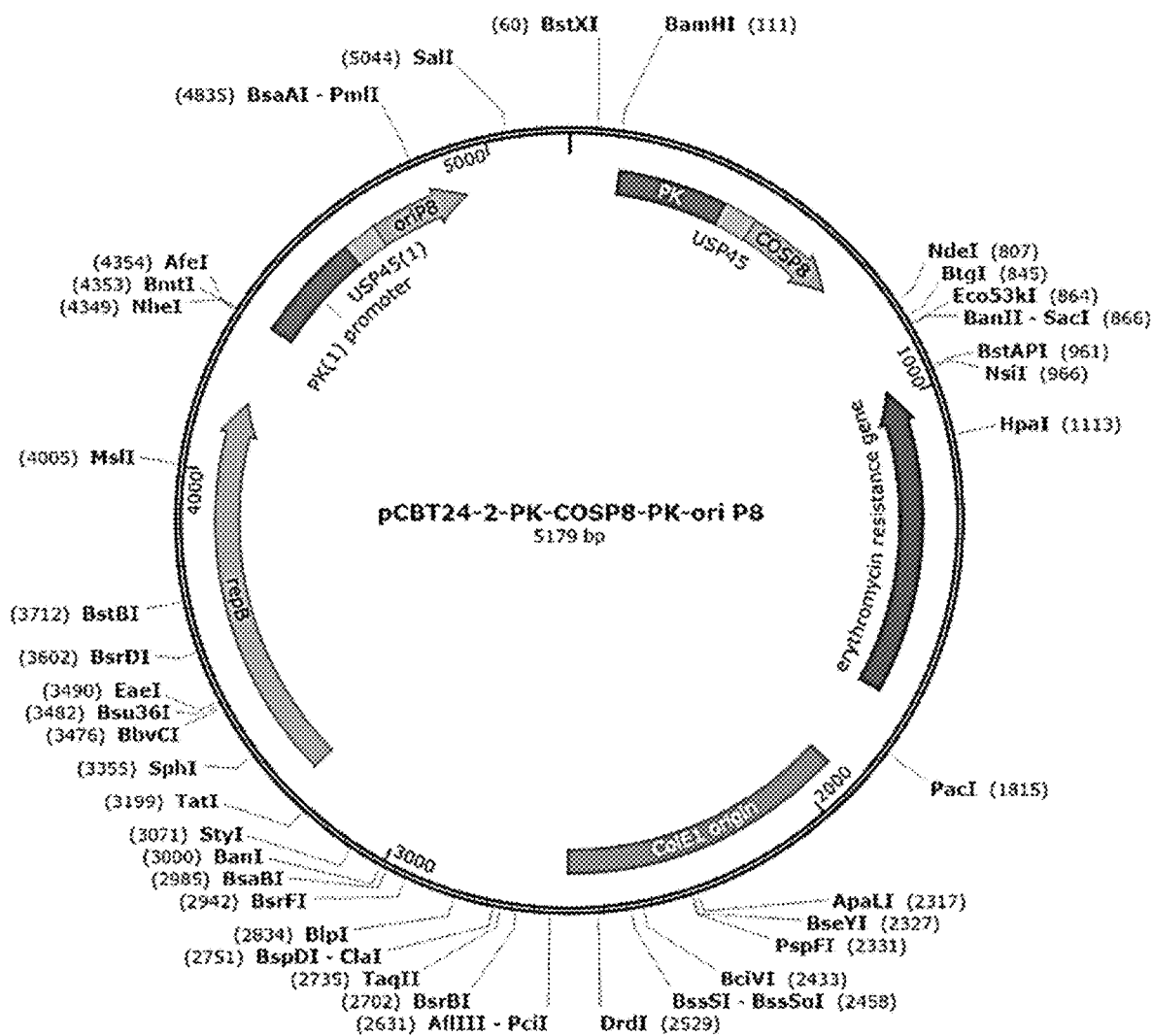
FIG. 3 is a cleavage map of an expression vector (pCBT24-2-P8) according to another embodiment of the present invention.

In a preferred embodiment, the expression vector of the present invention is an expression vector having a cleavage map of FIG. 2 or 3. The expression vector having the cleavage map of FIG. 2 is an expression vector including two promoters and having inserted therein a cystatin D-encoding gene as a heterologous nucleic acid, and the expression vector having the cleavage map of FIG. 3 is an expression vector including two promoters and having inserted therein a gene encoding the protein 8 (P8) having an anti-inflammatory activity.

The expression vector may be introduced into desired host cells by a method known in the art, for example, transfection, electroporation, microinjection, transduction, cell fusion, DEAE dextran, calcium phosphate precipitation, lipofection (lysosome fusion), use of a gene gun, or a DNA vector transporter (see, for example, Wu et al., J. Biol. Chem. 267:963 (1992); Wu et al., J. Biol. Chem. 263:14621 (1988); and Hartmut et al., Canadian Patent Application No. 2,012,311). Introduction of the expression vector may be performed using either a method known per se or any method which will be developed in the future.

A desired gene can be expressed and produced in a host cell or a microbial strain by introducing the expression vector including the gene expression vector of the present invention into the host cell and transfecting the host cell or microbial strain. To produce the desired protein by introducing the expression vector of the present invention, eukaryotic cells or prokaryotic cells may be used. Eukaryotic cells include cells, for example, established mammalian cells, probiotic cells, filamentous fungal cells and yeast cells, and prokaryotic cells include host cells, for example, *E. coli, Bacillus, Brevibacillus* cells, and the like.

The host cell may be a bacterial host cell belonging to the genus *Lactobacillus, Latococcus, Leuconostoc, Pediococcus,* or *Bifidobacterium*. The microbial strain is a strain belonging to the genus *Lactobacillus, Latococcus, Leuconostoc, Pediococcus,* or *Bifidobacterium*. Specific examples of the strain include, but are not necessarily limited to, *Lactobacillus rhamnosus, Lactobacillus acidophilus, Lactobacillus paracasei, Lactobacillus plantarum, Pediococcus pentosaceus,* or *Lactobacillus brevis* strains.

A desired protein may be produced by culturing the transformed host cell in vitro or in vivo. Culturing of the host cell is performed according to a known method. As a medium, a known culture method, such as DMEM, MEM, RPMI1640, IMDM, or the like, may be used. When the produced protein is a secreted protein, it may be purified from the medium, and when the produced protein is a non-secreted protein, it may be purified from the cell extract. For the production of a desired protein, a cell may be co-transfected with a plurality of vectors including other desired genes. In this case, a plurality of proteins can be produced at one time.

The present invention will be described in more detail below with reference to examples. However, these examples are for illustrative purposes only, and the scope of the present invention is not limited by these examples.

EXAMPLES

Example 1. Construction of System for Overexpression and Secretion of Lactic Acid Bacteria-Derived Protein Example 1-1. Selection of Promoters for Induction of Overexpression Five strong promoters (ChoS, L-carnitine, choline ABC transporter, permease protein; PK, pyruvate kinase; GK, glucokinase; G6Pi, glucose 6-phosphoate isomerase; and L-LDH, L-lactate dehydrogenase) for expression of a target protein (cystatin A) in lactic acid bacteria were selected from the glycolysis metabolic pathway. A host for expression of the target protein was *Pediococcus pentosaceus* SL4 (accession number: KCTC 10297BP), a patented strain. A previous experiment demonstrated that the glucose consumption rate of the host was very high, and HPLC analysis indicated that nearly 100% of the consumed glucose was converted to the secondary metabolite L-lactate. For this reason, of the promoters, five were selected from the glycolysis metabolic pathway, and two were selected from the secondary metabolite lactate production pathway.

Example 1-2. Construction of System for Overexpression and Secretion of Target Protein The plasmid pCBT24-2 (SEQ ID NO: 8) (KCCM12182P) was used. Each of the promoters selected in Example 1-1 was cloned into the DNA sequence encoding the usp45 secretion signal peptide (S) derived from *Lactococcus lactis*, thereby constructing DNA plasmids in the form of promoter (P)-secretion signal peptide-cystatin A (CyaA). BamHI/PstI restriction enzyme sites were inserted into each promoter ligated with the secretion signal peptide. The constructed plasmids were as follows:
pCBT24-2-ChoS-usp45-CysA,
pCBT24-2-PK-usp45-CysA,
pCBT24-2-GK-usp45-CyaA,
pCBT24-2-G6Pi-usp45-CysA, and
pCBT24-2-L-LDH-usp45-CysA.

Each of the constructed plasmids was transformed into *Pediococcus pentosaceus* SL4 (accession number: KCTC 10297BP). The level of expression/secretion induced by each of the promoters was measured, and then promoters showing high activities were combined with each other, thereby constructing pCBT24-2-G6Pi-usp45-CysA-usp45-G6Pi-CysA. The constructed DNA was transformed into *Pediococcus pentosaceus* SL4, and a transformant was selected. The transformant was mixed with LB liquid medium, and then cultured at 37° C. for 1 hour. After 1 hour of the culturing, the culture was plated onto LB agar medium containing erythromycin (final concentration: 10 μg/ml), and a strain showing resistance was first selected.

Example 1-3. Culture of *Pediococcus pentosaceus* SL4 Transformant

The transformant grown on MRS solid medium (agar plate) was inoculated into 10 ml of MRS liquid medium (containing 10 mg/ml of erythromycin) and statically cultured at 37° C. for 15 hours (overnight incubation). 1 ml of the culture was inoculated into 10 ml of M9 minimal medium (containing 10 mg/L of erythromycin), and then statically cultured at 37° C. for 48 hours. 5 ml of the culture was centrifuged, and the supernatant was collected. 5 ml of the supernatant was concentrated by TCA precipitation to isolate total protein. Using the total protein, the expression and secretion levels of cystatin A protein were comparatively analyzed by Western blotting. The microbial cells were diluted with buffer and lysed using a sonicator, and then the cell extract was analyzed by Western blotting, thereby determining the amount of cystatin A protein that was not secreted after expression.

Example 1-4. Isolation and Detection of Cystatin A Protein

Figure 4:
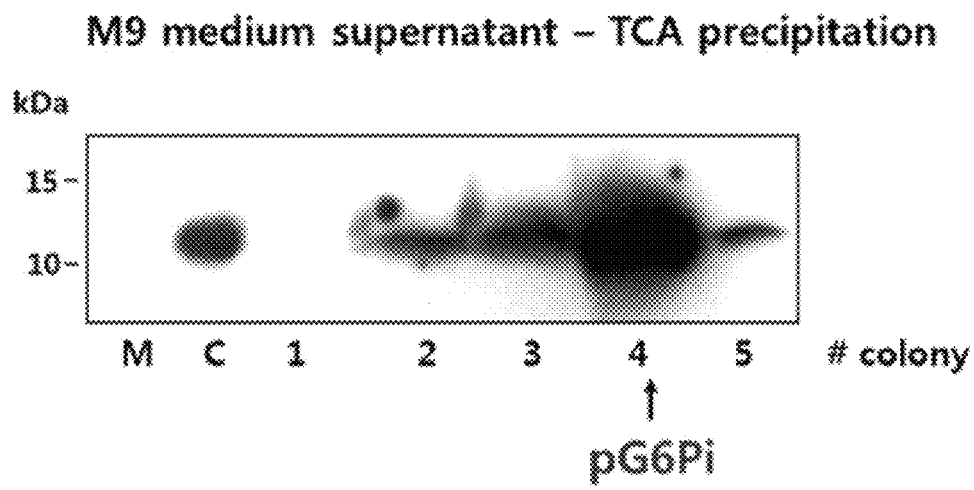
FIG. 4 is a photograph showing the results of Western blotting performed to qualitatively analyze the expression level of a cystatin A-encoding gene cloned into a gene expression cassette of the present invention.

The lactic acid bacteria transformant was cultured, and then 100% TCA (Trichloro Acetic Acid) was added to 5 ml of the culture supernatant to a final concentration of 20%. After mixing, the solution was incubated on ice for 30 minutes, and centrifuged at 15,000 rpm and 4° C. for 30 minutes to induce the precipitation of all proteins. After centrifugation, the supernatant was removed, and 200 μl of acetone was added to the precipitate which was then centrifuged at 15,000 rpm and 4° C., and the precipitated protein was washed. After the remaining acetone was completely removed by drying at room temperature, the secretion level of the target protein present in the culture supernatant was measured. The secretion level was measured by Western blotting, and the results of the measurement indicated that when the novel promoter was used, the expression/secretion levels significantly increased (see FIG. 4).

Example 2: Expression of P8 Protein 2-1. Cloning of P8 Protein-Encoding Gene Downstream of Chos Promoter The promoters selected in Example 1-1 were ligated with a usp45 signal peptide, and DNA fragments were synthesized using the ligated DNA sequences. BamHI/PstI restriction enzyme sites were inserted into each promoter ligated with the signal peptide, and usp45 was used as the secretion signal peptide. After completion of the synthesis, a portion of each promoter ligated with the signal peptide was digested with BamHI/PstI restriction enzymes, and the DNA fragments were isolated/purified by DNA gel extraction, and each of the DNA fragments was inserted into a pCBT24-2-P8/BamHI/PstI vector digested with the same restriction enzymes. For transformation, heat shock (at 42° C. for 45 sec) was used. An *E. coli* strain having erythromycin resistance was selected, thereby obtaining an *E. coli* transformant and the following cloned plasmids:
i) pCBT24-2-PK-P8,
ii) pCBT24-2-GK-P8,
iii) pCBT24-2-6PFK-P8,
iv) pCBT24-2-FK-P8,
v) pCBT24-2-G6Pi-P8,
vi) pCBT24-2-L-LDH-P8, and
vii) pCBT24-2-D-LDH-P8.

Each of the cloned plasmids was transformed into *Pediococcus pentosaceus* SL4. The levels of expression/secretion induced by each of the promoters were measured, and then promoters showing high activities were combined with each other, thereby constructing pCBT24-2-GK-P8-L-LDH-oriP8, pCBT24-2-PK-P8-PK-oriP8, and pCBT24-2-GK-P8-GK-oriP8.

The constructed gene expression cassettes were transformed onto *Pediococcus pentosaceus* SL4, and a transformant was selected. Transformation was performed as follows. A medium component was removed from cultured cells, and only clean cells were collected and electroporated using a Gene Pulser (Bio-Rad) under the conditions of 2000 V, 25 μF and 200Ω. The plasmid used in transformation was pCBT24-2 (KCCM12182P) of SEQ ID NO: 9, and a transformant was obtained by selecting *Pediococcus pentosaceus* having erythromycin resistance.

Example 2-2. Culture of *Pediococcus pentosaceus* SL4 Transformant

The transformant grown on MRS solid medium was inoculated into 10 ml of MRS liquid medium (containing 10 mg/L of erythromycin) and statically cultured at 37° C. for 17 hours. 1 ml of the culture was inoculated into 10 ml of M9 minimal medium (containing 10 mg/L of erythromycin), and then statically cultured at 37° C. for 48 hours. After culturing, the M9 medium was centrifuged, and the supernatant and the cells were collected. A portion of the supernatant was used for quantitative analysis of P8, and the remaining portion of the supernatant was concentrated by TCA precipitation to isolate all proteins. Using the proteins, the expression/secretion levels of P8 were comparatively analyzed by Western blotting. Meanwhile, the cells were diluted in a suitable amount of buffer and lysed using a sonicator, after which the cell extract was collected, and then the expression/secretion levels of P8 were qualitatively analyzed by Western blotting.

Example 2-3. Isolation and Detection of P8 Protein

Figure 5:
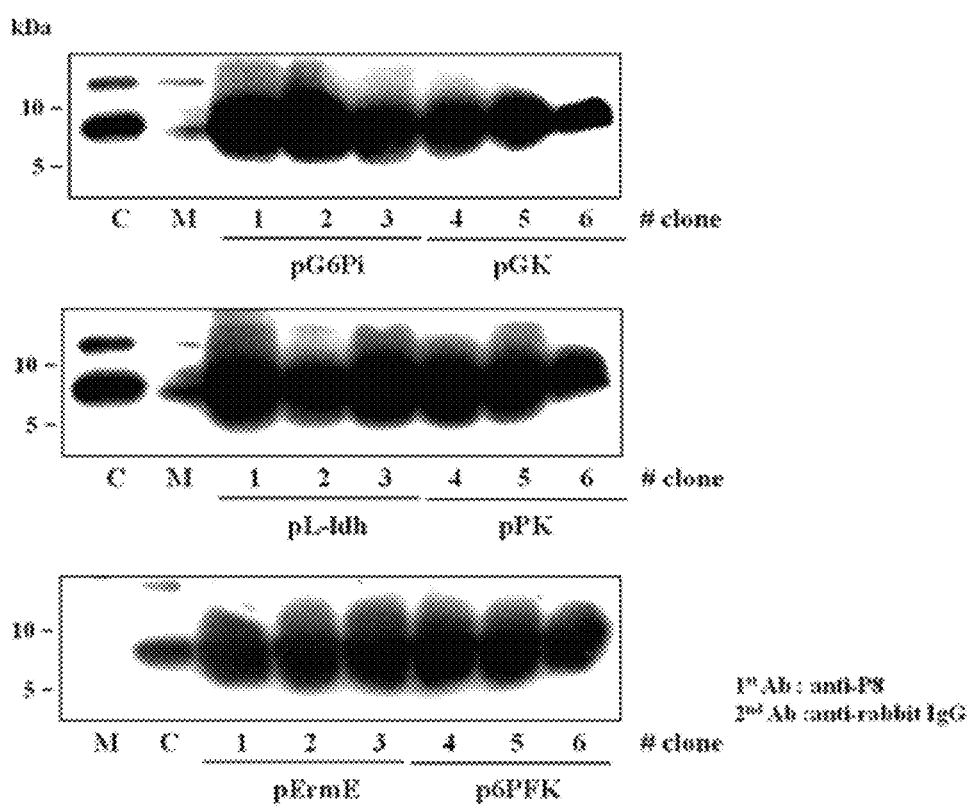
FIG. 5 is a graph showing the results of Western blotting performed to quantitatively analyze the changes in expression/secretion levels of P8 protein by a gene expression cassette of the present invention.
Figure 6:
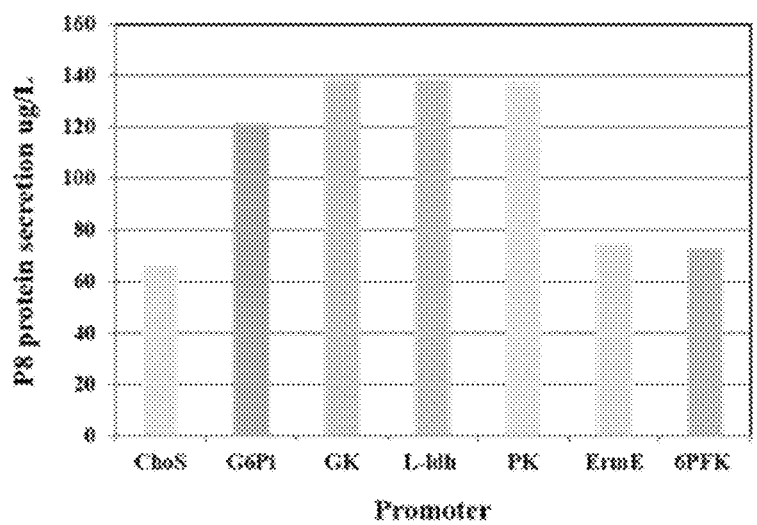
FIG. 6 is a graph showing the results of ELISA performed to quantitatively analyze the changes in expression/secretion levels of P8 protein by a gene expression cassette of the present invention.

The *Pediococcus pentosaceus* SL4 transformant was cultured, and then TCA (Trichloro Acetic Acid) was added to the culture supernatant at a ratio of 1:4 to a final concentration of 20%. After mixing, the solution was incubated at low temperature (0 to 4° C.) for 30 minutes, and centrifuged at 15,000 rpm and 4° C. for 30 minutes to induce the precipitation of all proteins. After centrifugation, the supernatant was removed, and acetone having a volume corresponding to $\frac{1}{10}$ of the initially used culture supernatant was added to the remaining precipitate which was then centrifuged at 14,000 rpm and 4° C. for 30 minutes, and the precipitated protein was washed. After the remaining acetone was completely removed by drying at room temperature, and the residue was used for measurement of expression/secretion levels. The expression/secretion levels were measured by Western blotting. FIG. 5 shows the results of Western blotting performed to qualitatively analyze the changes in expression/secretion levels of P8 protein by the gene expression cassette of the present invention, and FIG. 6 is a graph showing the results of ELISA performed to quantitatively analyze the changes in expression/secretion levels of P8 protein by a gene expression cassette of the present invention. As shown in FIGS. 5 and 6, the results of measurement of the secretion level indicated that the use of the gene expression cassette of the present invention significantly increased the expression/secretion levels.

Figure 7:
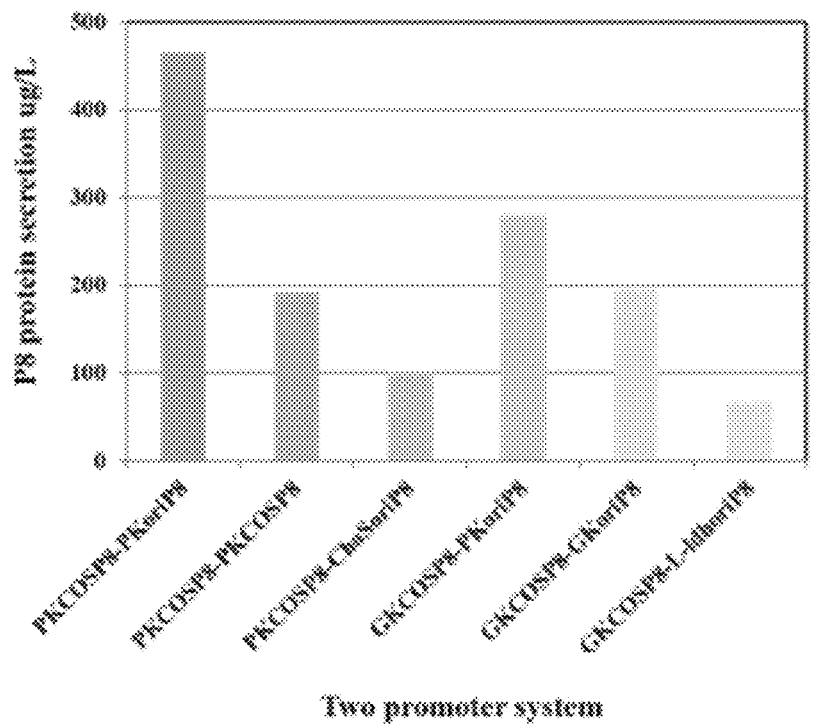
FIG. 7 is a photograph showing the results of Western blotting performed to qualitatively analyze the changes in expression/secretion levels of P8 protein by a gene expression cassette of the present invention.
Figure 7:
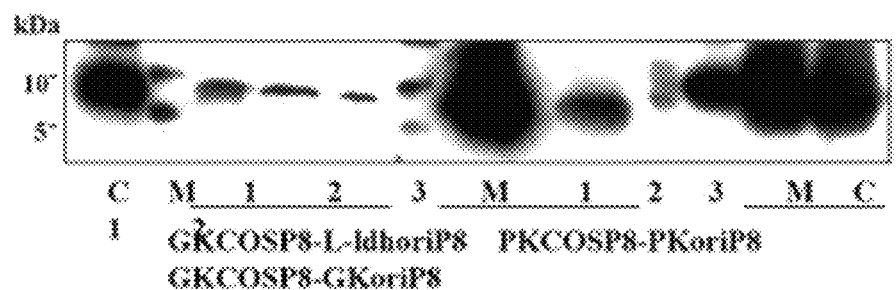

FIG. 7 is a photograph showing the results of Western blotting performed to quantitatively analyze the changes in expression/secretion levels of P8 protein by the gene expression cassette including a combination of two promoters (PK-PK). As shown in FIG. 7, the results of measuring the expression/secretion levels of P8 in pCBT24-2-PK-P8-PK-oriP8 constructed by inserting PK-oriP8 into pCBT24-2-PK-P8 showing the highest expression/secretion levels indicated that the secretion level of P8 increased up to about 466 μg/L.

Example 3: Expression of P14 Protein 3-1. Cloning of P14 Protein-Encoding Gene Downstream of G6Pi Promoter The promoters selected in Example 1-1 were ligated with a usp45 signal peptide, and DNA fragments were synthesized using the ligated DNA sequences. BamHI/PstI restriction enzyme sites were inserted into each promoter ligated with the signal peptide. After completion of the synthesis, a portion of each promoter ligated with the signal peptide was digested with BamHI/PstI restriction enzymes, and the DNA fragments were isolated/purified by DNA gel extraction. Each of the DNA fragments was inserted into a pCBT24-2-P14/BamHI/PstI vector digested with the same restriction enzymes. The constructed pCBT24-2-G6Pi-P14 was transformed into *Pediococcus pentosaceus* SL4 in the same manner as described in Example 1. The levels of expression/secretion induced by each of the promoters were measured, and then promoters showing high activities were combined with each other, thereby constructing pCBT24-2-G6Pi-P14-L-LDH-oriP14. A transformant was selected on antibiotic-containing medium (LB liquid medium containing 20 μg/ml of kanamycin).

Example 3-2. Culture of *Pediococcus pentosaceus* SL4 Transformant

The transformant grown on MRS solid medium was inoculated into 10 ml of MRS liquid medium (containing 10 mg/ml of erythromycin) and statically cultured at 37° C. for 48 hours. After 48 hours, 1 ml of the MRS EM medium was inoculated into 10 ml of M9 minimal medium (containing 10 mg/L of erythromycin), and then statically cultured at 37° C. for 48 hours. After culturing, 5 ml of the M9 medium was centrifuged, and the supernatant and the cells were collected. A portion of the supernatant was used for quantitative analysis of P14, and the remaining portion of the supernatant was concentrated by TCA precipitation to isolate all proteins. Using the proteins, the expression/secretion levels of P14 were comparatively analyzed by Western blotting. Meanwhile, the cells were diluted in a suitable amount of buffer and lysed using a sonicator, after which the cell extract was collected, and then the expression/secretion levels of P14 were qualitatively analyzed by Western blotting.

Example 3-3. Isolation and Detection of P14 Protein

The lactic acid bacteria transformant was cultured, and then 100% TCA (Trichloro Acetic Acid) was added to the culture supernatant to a final concentration of 20%. After mixing, the solution was incubated on ice for 30 minutes, and centrifuged at 14,000 rpm and 4° C. for 30 minutes to induce the precipitation of all proteins. After centrifugation, the supernatant was removed, and acetone having a volume corresponding to $\frac{1}{10}$ of the initially used culture supernatant was added to the remaining precipitate which was then centrifuged at 14,000 rpm and 4° C. for 30 minutes, and the precipitated protein was washed. After the remaining acetone was completely removed by drying at room temperature, and the residue was used for measurement of expression/secretion levels. The expression/secretion levels were measured by Western blotting.

Figure 8:
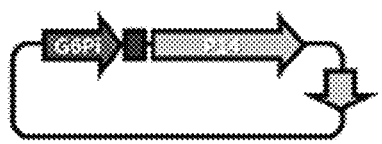
FIG. 8 is a photograph showing the results of Western blotting performed to qualitatively analyze the changes in expression/secretion levels of P14 protein by a gene expression cassette of the present invention.
Figure 8:
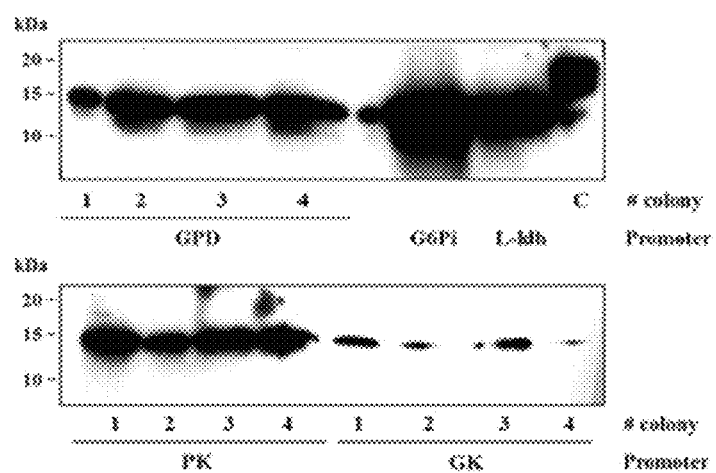

FIG. 8 is a photograph showing the results of Western blotting performed to qualitatively analyze the changes in expression/secretion levels of P14 protein by the gene expression cassette including the G6Pi promoter. As shown in FIG. 8, the results of measuring the expression/secretion levels of P14 in pCBT24-2-G6Pi-P14-PK-oriP14 constructed by inserting PK-oriP14 into pCBT24-2-G6Pi-P14 showing the highest expression/secretion levels indicated that the secretion level of P14 was high.

INDUSTRIAL APPLICABILITY

The gene expression cassettes according to various embodiments of the present invention enable a desired protein to be highly expressed by gene expression and to be produced in large amounts, regardless of the type of cell, the kind of gene, and the kind of transfection reagent. These gene expression cassettes may be widely applied not only as a reagent in the field of biotechnology, but also as a therapeutic protein drug, or for treatment, inspection and diagnosis using genes in clinical tests.

Although the preferred embodiments of the present invention have been described in detail, the present invention is not limited to the above-described embodiments. Those skilled in the art to which the present invention pertains will appreciate that various modifications and alterations may be easily made based on the above-described embodiments. Therefore, the true scope of protection of the present invention should be defined based on the appended claims and their equivalents.

The invention claimed is:

1. A gene expression cassette comprising:
at least one promoter operably linked to a heterologous nucleic acid encoding a biologically active polypeptide selected from the group consisting of SEQ ID NO: 1 to SEQ ID NO: 8;
a nucleic acid sequence encoding a secretion signal peptide; and
a selective marker gene.

2. The gene expression cassette of claim 1, further comprising downstream of the at least one promoter, a second promoter, a second secretion signal peptide, and a second heterologous nucleic acid sequence.

3. The gene expression cassette of claim 2, wherein the second promoter is identical to or different from the at least one promoter, and the second heterologous nucleic acid sequence is identical to or different from the heterologous nucleic acid sequence.

4. The gene expression cassette of claim 1, wherein the selective marker gene is an antibiotic resistance gene.

5. The gene expression cassette of claim 1, wherein the nucleic acid sequence encoding the secretion signal peptide is selected from the group consisting of a USP45 secretion signal peptide encoding sequence, Usp45 N4 encoding sequence, and a *Lactobacillus brevis* S-layer protein signal peptide encoding sequence.

6. The gene expression cassette of claim 1, further comprising a replication origin for replication in a microbial strain.

7. The gene expression cassette of claim 6, wherein the replication origin is selected from the group consisting of ColE1, Ori, and oriT.

8. The gene expression cassette of claim 1, wherein the heterologous nucleic acid is selected from the group consisting of genes that encode hormones, cytokines, enzymes, coagulation factors, transporter proteins, receptors, regulatory proteins, structural proteins, transcription factors, antigens, and antibodies.

9. An expression vector comprising the gene expression cassette of claim 1.

10. A microbial strain transformed with the expression vector of claim 9.

11. The strain of claim 10, which is a strain belonging to the genus *Lactobacillus, Leuconostoc, Pediococcus,* or *Bifidobacterium*.

12. The strain of claim 11, which is a *Lactobacillus rhamnosus, Lactobacillus acidophilus, Lactobacillus paracasei, Lactobacillus plantarum, Pediococcus pentosaceus,* or *Lactobacillus brevis* strain.

13. The strain of claim 12, which is the *Pediococcus pentosaceus* SL4 strain deposited as KCTC 10297BP.

* * * * *